United States Patent [19]
Garrett et al.

[11] Patent Number: 5,427,338
[45] Date of Patent: Jun. 27, 1995

[54] INTRAVENOUS AND TRANSDUCER LINE ORGANIZER

[75] Inventors: Shirley M. Garrett, Derby; Conrad H. Boettger, Hesston, both of Kans.

[73] Assignee: St. Francis Research Institute, Wichita, Kans.

[21] Appl. No.: 139,210

[22] Filed: Oct. 19, 1993

[51] Int. Cl.⁶ .............................................. F16L 3/22
[52] U.S. Cl. ................... 248/68.1; 5/503.1; 128/DIG. 6
[58] Field of Search ............... 248/68.1, 74.2; 5/658, 5/503.1; 24/16 PB; 604/80; 128/DIG. 6

[56] References Cited

U.S. PATENT DOCUMENTS

| | | | |
|---|---|---|---|
| D. 285,789 | 9/1986 | Wright et al. | |
| 4,125,490 | 11/1978 | Hettinga | |
| 4,571,845 | 2/1986 | Wright et al. | |
| 4,690,674 | 9/1987 | Dalglish | 128/DIG. 6 X |
| 4,795,429 | 1/1989 | Feldstein | 604/80 |
| 4,988,062 | 1/1991 | London | 248/68.1 |
| 5,138,134 | 8/1992 | Ellison | 248/476 X |
| 5,224,674 | 7/1993 | Simons | 248/68.1 |
| 5,254,110 | 10/1993 | Marcus et al. | 248/68.1 X |

FOREIGN PATENT DOCUMENTS

| | | | |
|---|---|---|---|
| 1232753 | 2/1988 | Canada . | |
| 3506397 | 8/1986 | Germany | 248/68.1 |

*Primary Examiner*—Ramon O. Ramirez
*Attorney, Agent, or Firm*—Hovey, Williams, Timmons & Collins

[57] ABSTRACT

An organizing device (10) is provided for use in hospitals, in order to maintain plural patient care lines (e.g., transducer lines (50) and intravenous infusion lines (52)) in a separate, individually identified, easy to use relationship. The device (10) includes an elongated, rigid base plate (12) having upstanding wall sections (14); the wall sections (14) include axially spaced apart, differently configured openings (34, 36) for receiving different patient care lines (50, 52). The base plate (12) also has a surface (28) for receiving line-identifying information thereon. A level indicator (16), viewable from both sides of the device (10), is provided in order to facilitate proper setup of transducer lines (50). The device (10) is preferably of unitary and integral synthetic resin construction, and is of a length to span the distance between upstanding hospital bed rails (58), thereby permitting releasable connection of the device (10) to a hospital bed.

8 Claims, 2 Drawing Sheets

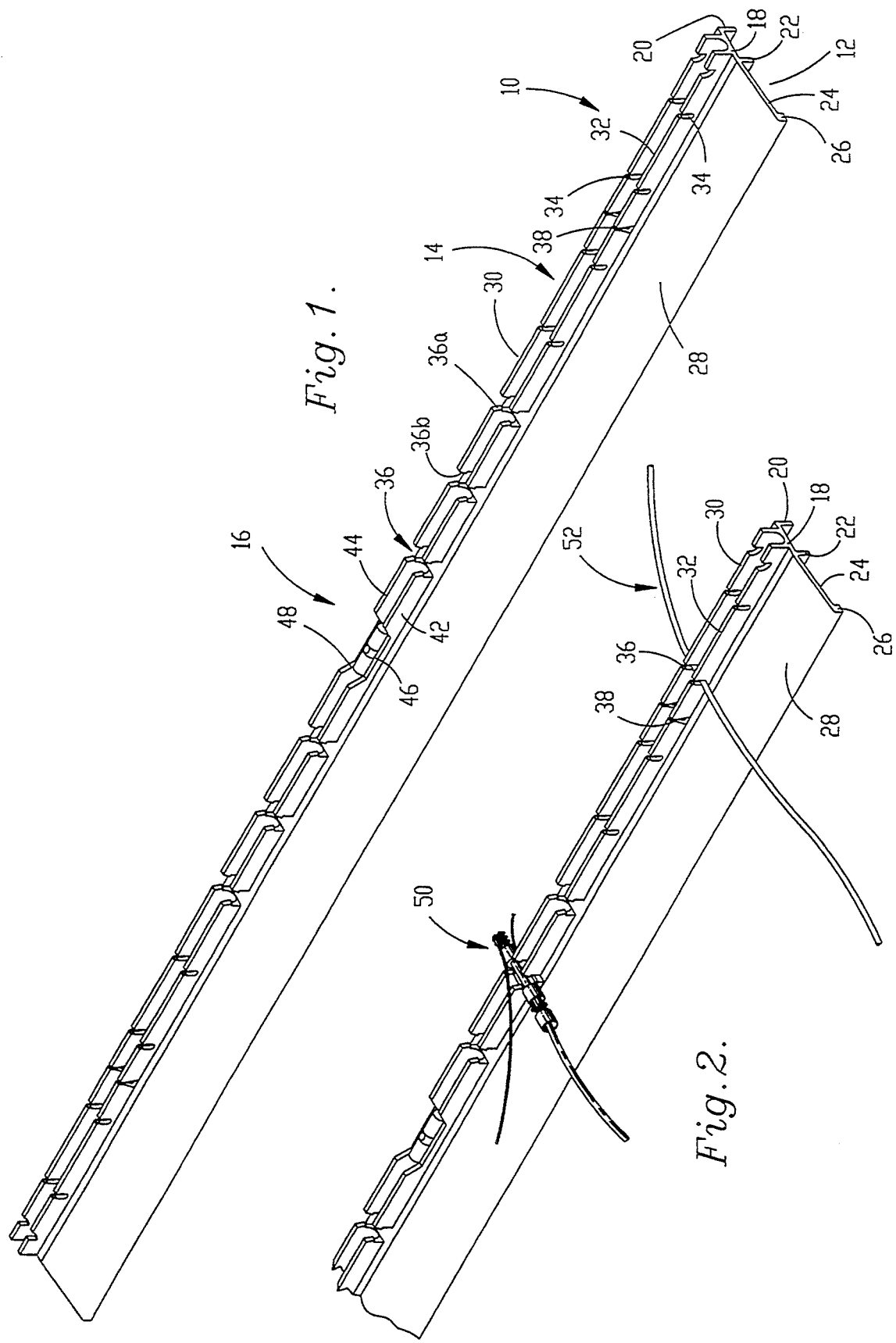

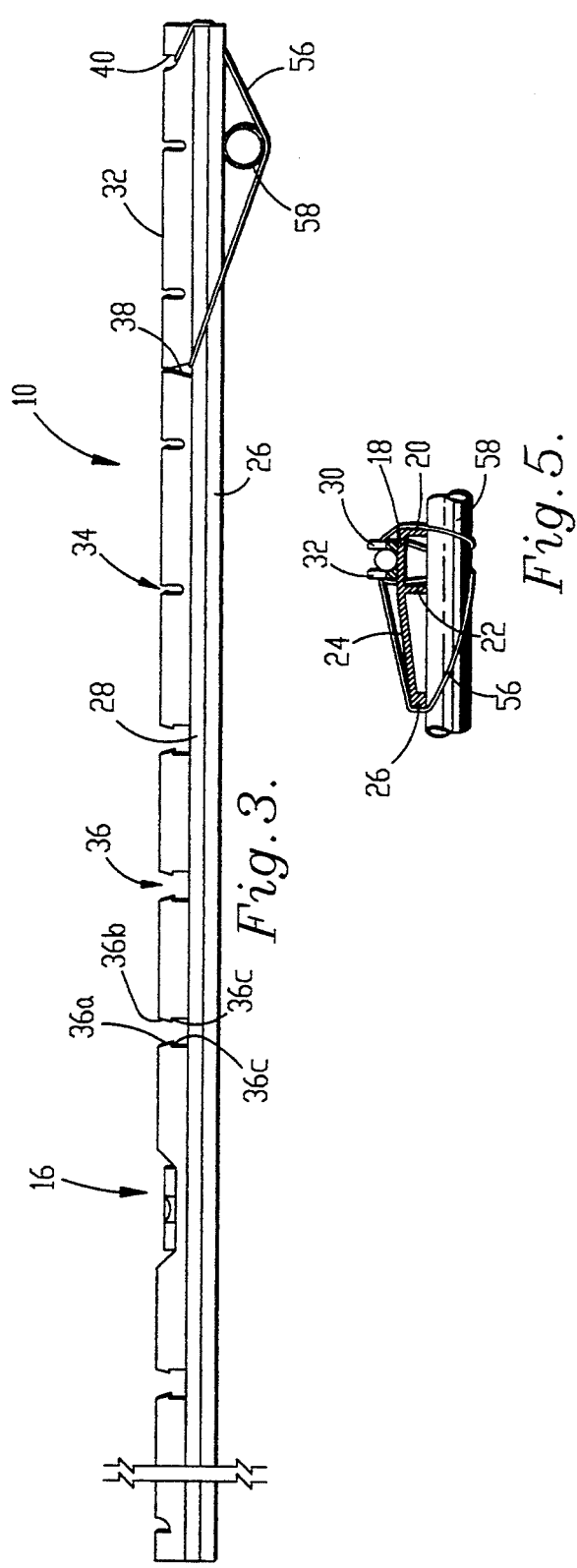
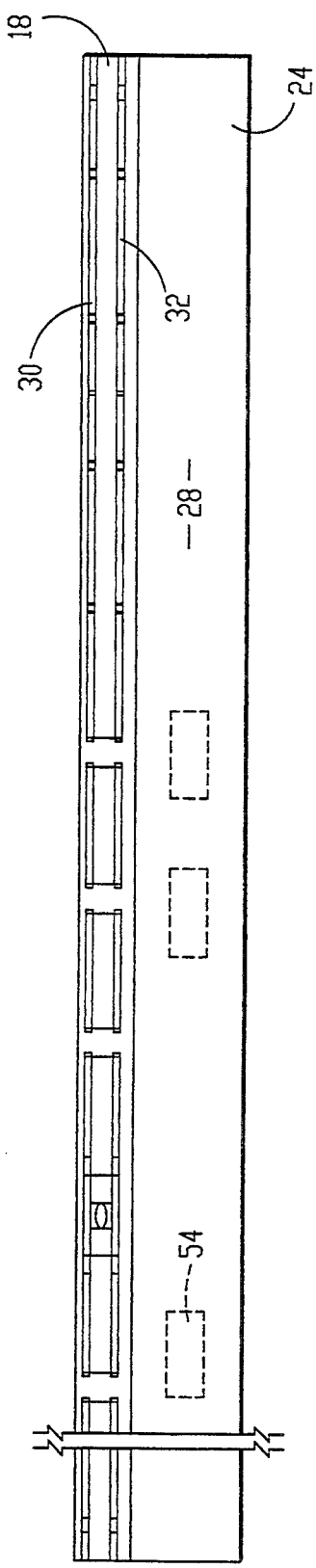

INTRAVENOUS AND TRANSDUCER LINE ORGANIZER

BACKGROUND OF THE INVENTION

1. Field of the Invention

The present invention is broadly concerned with a light-weight organizing device usable in operating rooms, post-operative wards and in transporting critical patents throughout health care systems for maintaining proper organization and labeling of various multiple patient care lines such as transducer housings and intravenous infusion lines. More particularly, the invention pertains to such an organizing device including an elongated rigid body, preferably of length to span the distance between upstanding side rails of a conventional hospital bed or transportation gurney, with the body having a base plate supporting spaced apart, upstanding wall sections with line-receiving openings therebetween; the openings are configured for releasably and frictionally retaining therein differently configured patient care lines without interruption of IV flow or data readings, with the latter extending transverse to the longitudinal axis of the body. In order to enable and insure proper level orientation, balancing and calibration of the transducer lines upon arrival in the post-care unit, a central indicator is preferably provided on the device.

2. Description of the Prior Art

Hospital anesthesia, recovery and critical care staffs are often confronted with the problem of properly organizing and labeling relatively large numbers of patient care lines secured to a patient undergoing major surgery and recovery. Such patient care lines would normally include one or more transducers and intravenous infusion lines. For example, during transport of a patient from an operating room, recovery ward, critical care unit or throughout health care systems, the patient's condition may warrant adjustments in infusion rates of life-supporting medications, and it is important that these critical adjustments be made both accurately, correctly and in a timely way. In the present situation, however, the plural patient care lines can easily become tangled and disconnected possibly interrupting a life-supporting medication infusion which is very difficult or impossible to quickly and accurately locate and adjust, particularly during patient transfer.

In addition, whenever transducers are used, part of the setup procedure is to balance and calibrate the transducer lines, so that oscilloscope readings are accurate. This requires that the practitioner have an available leveling device to insure that the transducers are level with the mid-axillary line [phlebostatic axis]. Experience has proved that it is difficult to keep these leveling devices in each room or otherwise handy, and as a result they become difficult to locate when needed. Leveling devices are known (U.S. Pat. No. 4,571,845), but these provide no aid in organizing and labeling the many and easily tangled patient care lines incidental to anesthesia, major operations, and recovery.

SUMMARY OF THE INVENTION

The present invention overcomes the problems outlined above and provides a greatly improved device for organizing plural patient care lines. Broadly speaking, the device of the invention includes an elongated, rigid body presenting a base plate having a plurality of upstanding, spaced apart wall sections extending upwardly from the base plate with line-receiving openings therebetween, such openings being axially spaced along the length of the body. The non-occlusive line-receiving openings are configured for releasably and frictionally retaining therein a plurality of differently configured patient care lines, with these lines extending transverse to the longitudinal axis of the body and being cooperatively supported by the base plate and the frictional engagement between the individual lines and the adjacent upstanding margins of the opening-defining wall sections. In order to insure proper labeling, the upper surface of the base plate is configured for receiving line-identifying information thereon.

The device is preferably of a length to span the distance between side rails of a conventional hospital bed or transportation gurney, thereby permitting releasable connection of the device to such side rails. In this orientation, the various patient care lines can be individually positioned within the appropriate line-receiving openings of the device, and each line can be individually labeled. In this way, all of the patient care lines are prevented from kinking or tangling and moreover the identity of each line is readily available to the hospital staff.

The preferred device also includes a level indicator at the central region thereof, which facilitates calibration of transducer lines.

BRIEF DESCRIPTION OF THE DRAWINGS

FIG. 1 is an isometric view of the preferred organizing device of the invention;

FIG. 2 is a fragmentary isometric view similar to that of FIG. 1, but illustrating placement of a transducer and intravenous infusion line in appropriate line-receiving openings of the device;

FIG. 3 is a side view of the organizing device of the invention, shown with one end thereof releasably secured to a hospital bed side rail;

FIG. 4 is a plan view of the device illustrated in FIG. 4; and

FIG. 5 is an end view depicting the releasable connection of the device to a hospital bed side rail.

DETAILED DESCRIPTION OF THE PREFERRED EMBODIMENTS

Turning now to the drawings, and particularly FIG. 1, an organizing device 10 is illustrated. Broadly speaking, the device 10 includes a base plate 12 as well as upstanding wall sections 14 and central horizontal level indicating device 16. The device 10 is preferably of unitary and integral construction, and is advantageously formed of a rigid synthetic resin material. The device 10 typically would have a length of from about 30–40 inches and a width of from about 2–6 inches; these dimensions are variable, but preferably the length of the device should be sufficient to span the distance between upstanding side rails of a normal hospital bed or transportation gurney.

In more detail, the base plate 12 includes a generally horizontal rear segment 18 having a pair of closely spaced apart, depending feet 20, 22 extending the full length thereof. Additionally, the base plate 12 presents an inclined forward segment 24 terminating in a depending foot 26 extending the full length thereof. The forward segment 24 presents an upper surface 28 designed to receive line-identifying information thereon as will be explained below.

The wall sections 14 extend upwardly from rear segment 18 and include identically configured, laterally parallel spaced apart, upstanding wall members 30, 32 wherein the rear segment and the wall members form a generally U-shaped channel extending perpendicularly upwardly from the base plate 12. Each such wall member 30, 32 has, at spaced locations along the length thereof, openings 34 and 36 which are designed to non-occlusively receive, respectively, intravenous infusion lines and transducer lines. The openings 34 and 36 of each wall member are aligned as shown. As illustrated in FIG. 1 the openings 34 and 35 are spaced apart a distance greater than the width of the openings. As best illustrated in FIG. 1, each of the wall members 30, 32 has a total of six transducer line openings 36 in the central region of the body and an additional three of the infusion line-receiving openings 34 on each outboard end of the body. It will be noted in this respect that each of the openings 36 is defined by opposed margins 36a, 36b, each of these having a notch 36c therein. On the other hand, each of the openings 34 is generally U-shaped or tear-shaped in configuration and does not extend to the segment 18. As best viewed in FIG. 3, the extreme ends of the wall members 30, 32 have specialized openings 38, 40 therein for permitting releasable attachment of the device 10 to a hospital bed.

The centermost portions 42, 44 of the wall members 30, 32 are configured to cooperatively receive therebetween the leveling device 16. In particular, it will be observed that the portions 42, 44 include relieved zones 46, 48, with the level indicator 16 being situated between the wall members at these relieved zones. In this fashion, the level indicator, which is of the conventional "bubble" variety, can be observed from both sides of the device 10, and from above, facilitating readability in tight places.

FIG. 2 illustrates the attachment of a transducer housing 50 within a pair of aligned openings 36, and also attachment of an intravenous infusion line 52 within an appropriately configured pair of aligned openings 36. With these exemplary lines so positioned, the user may then appropriately label each of the lines, either by writing directly on surface 28, or by attachment of removable labels 54 onto the surface 28 (see FIG. 4). Those skilled in the art will readily appreciate that the device 10 can accommodate a large number of such lines, and all would be maintained in proper spaced apart, properly labeled relationship facilitating the health care professional's ability to provide momentary critical assessments and accurate adjustments of monitored infusions and data and to prevent disconnections.

When a patient is removed to a recovery ward, it is generally preferred to releasably secure the device 10 to the side rails of the patient's hospital bed. As best shown in FIGS. 3 and 5, an elastomeric band 56 can be employed to extend around a hospital bed rail 58 and be secured within the specialized openings 38, 40. This procedure is repeated at both ends of the device 10, so as to releasably but fixedly secure the device in spanning relationship to the bed side rails facilitating ready access to the patient in an emergency situation.

If desired, the rear surface of the depending foot 20 may be provided with measuring markings and/or conversion charts. Such indicia is preferably molded into the foot 20 during manufacture. In addition, if desired, a vertical level-indicating device can also be provided with the body 10.

We claim:

1. A device for organizing a plurality of patient care lines, consisting essentially of:
   an elongated, rigid body presenting a base plate and a plurality of upstanding substantially parallel, spaced apart wall sections extending substantially perpendicularly upwardly from said base plate with non-occluding, line-receiving openings therebetween, said non-occluding openings being axially spaced along the length of said body, said openings being spaced apart a distance greater than the width of said openings, said base plate and said wall sections forming a generally U-shaped channel which is open at the top,
   said non-occluding, line-receiving openings being configured for releasably and frictionally retaining therein a plurality of differently configured patient care lines, with said lines extending transverse to the longitudinal axis of said body and being cooperatively supported by said base plate and the frictional engagement between the individual lines and the adjacent upstanding margins of said opening-defining wall sections,
   said base plate including a planar forward segment extending transverse to the longitudinal axis of said body and defining an upper surface for supporting said lines and for receiving line-identifying information thereon, said forward segment upper surface being visible between said lines, said forward segment having a transverse width substantially greater than said wall sections and extending substantially the entire length of said base plate.

2. The device of claim 1, there being a pair of upstanding, closely adjacent, laterally spaced apart wall sections each extending upwardly from said base plate and having aligned openings therein, said aligned openings cooperatively defining said non-occluding, line-receiving openings.

3. The device of claim 1, at least certain of said openings being configured for receiving a transducer housing, others of said non-occluding openings being configured for receiving intravenous infusion lines.

4. The device of claim 1, said body being of a length to span the distance between side rails of a hospital bed or transportation gurney, there being means for releasably securing said body to said side rails.

5. The device of claim 4, said securing means comprising a pair of elastomeric bands.

6. The device of claim 1, including a level indicator supported on said body adjacent said upstanding wall sections.

7. The device of claim 1, including elongated, depending, side marginal feet extending downwardly from said base plate.

8. The device of claim 1, said body being unitary and integral.

* * * * *